United States Patent
Tanahashi et al.

(10) Patent No.: US 9,226,997 B2
(45) Date of Patent: Jan. 5, 2016

(54) BIODEGRADABLE PARTICLE AND METHOD FOR PRODUCING THE SAME

(75) Inventors: Kazuhiro Tanahashi, Otsu (JP); Megumi Nakanishi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 455 days.

(21) Appl. No.: 13/402,851

(22) Filed: Feb. 22, 2012

(65) Prior Publication Data

US 2012/0156302 A1     Jun. 21, 2012

Related U.S. Application Data

(63) Continuation of application No. 12/084,102, filed as application No. PCT/JP2006/321432 on Oct. 26, 2006, now abandoned.

(30) Foreign Application Priority Data

Oct. 27, 2005  (JP) ................................ 2005-312474
Oct. 27, 2005  (JP) ................................ 2005-312476
Mar. 31, 2006  (JP) ................................ 2006-097171

(51) Int. Cl.

| | |
|---|---|
| *A61K 9/14* | (2006.01) |
| *A61L 31/14* | (2006.01) |
| *A61K 9/00* | (2006.01) |
| *A61L 24/00* | (2006.01) |
| *A61L 24/04* | (2006.01) |
| *A61L 31/06* | (2006.01) |
| *C08J 3/12* | (2006.01) |
| *C08L 67/04* | (2006.01) |
| *C08L 71/02* | (2006.01) |

(52) U.S. Cl.
CPC ............. *A61L 31/148* (2013.01); *A61K 9/0019* (2013.01); *A61K 9/14* (2013.01); *A61L 24/0042* (2013.01); *A61L 24/046* (2013.01); *A61L 31/06* (2013.01); *C08J 3/12* (2013.01); *C08L 67/04* (2013.01); *A61L 2430/36* (2013.01); *C08J 2367/04* (2013.01); *C08L 71/02* (2013.01)

(58) Field of Classification Search
None
See application file for complete search history.

(56) References Cited

U.S. PATENT DOCUMENTS

| 5,543,158 A | 8/1996 | Gref et al. ...................... 424/501 |
| 2004/0096662 A1 * | 5/2004 | Lanphere et al. ............. 428/402 |
| 2005/0175709 A1 * | 8/2005 | Baty et al. ...................... 424/489 |
| 2006/0069168 A1 * | 3/2006 | Tabata et al. ............... 514/772.1 |

FOREIGN PATENT DOCUMENTS

| JP | 9-511002 A | 11/1997 |
| JP | 2004-167229 A | 6/2004 |
| JP | 2004-313759 A | 11/2004 |
| WO | WO 2004039425 A1 * | 5/2004 |

OTHER PUBLICATIONS

T. Riley et al., "Colloidal stability and drug incorporation aspects of micellar-like PLA-PEG nanoparticles." Colloids and Surfaces B: Biointerfaces, vol. 16, 1999, pp. 147-159.

Y.M. Kwon et al., "Biodegradable Triblock Copolymer Microspheres Based on Thermosensitive Sol-Gel Transition", Pharmaceutical Research, vol. 21 No. 2, Feb. 2004, pp. 339-343.

* cited by examiner

*Primary Examiner* — Isaac Shomer

(74) *Attorney, Agent, or Firm* — Kubovcik & Kubovcik

(57) ABSTRACT

The present invention aims to provide a biodegradable particle capable of being molded without an aggregation or cohesion of the particles, capable of being carried or injected without clogging by an aggregation in a micro diameter tube such as of a catheter, needle or syringe mainly used in pharmaceutical and medical applications of which inner diameter is smaller than the particle size or in a blood vessel and capable of being smoothly degraded in a specified period of time so that degraded component can finally be absorbed or discharged in vitro. As means for solving the problem, the present invention provides a biodegradable particle characterized in that a compressive modulus of the particle in water saturated state is 10 MPa or less.

4 Claims, No Drawings

BIODEGRADABLE PARTICLE AND METHOD FOR PRODUCING THE SAME

This application is a continuation of application Ser. No. 12/084,102, filed Mar. 2, 2009 now abandoned, which is a 371 of international application PCT/JP2006/321432, filed Oct. 26, 2006, which claims priority based on Japanese Patent Application Nos. 2005-312474, 2005-312476 and 2006-097171, filed Oct. 27, 2005, Oct. 27, 2005, and Mar. 31, 2006, respectively, and which are incorporated herein by reference.

TECHNICAL FIELD

The present invention relates to a biodegradable spherical particle which can be carried through tubes having a micro diameter smaller than the particle size, such as of catheter, needle or injector which are pharmaceutical and medical devices.

BACKGROUND ART

In medical field, safety of therapy or minimum invasive therapy which is light in patient's pain has become important. Along with that, techniques for designing or synthesizing safer materials or techniques for administration in vivo have been developed. One of them is technique of therapy or administration of drug through a tube of small inner diameter. By being the inner diameter of the tube small, it became unnecessary to incise patient's body, and a pain accompanied by inserting the tube into body was also greatly reduced. Therapy by catheter is a marked example of that. Another one is a technology relating to a biodegradable or bioabsorbable material which is not left in the body. A sewing thread or orthopaedic material made such as of polylactic acid, polyglycolic acid or polycaprolactone is used also in clinical site, and recently, many research results of regenerative medicine in which these materials were applied were reported. As to polymer particle which is degradable or absorbable in the body is also known mainly as a carrier of drugs (refer to Patent references 1 and 2).

Furthermore, at an incision accompanied by a surgical operation such as of liver, by injecting an embolization material into blood vessel beforehand, it is possible to firmly and quickly stanch to minimize bleeding. And, as a technique or therapy in which such embolization material is used, other applications than the prevention of bleeding, an application to an artery embolization in which nutrition for an unrecectable tumor is intercepted by hemostasis, and further, a chemical embolization therapy in which an anticancer drug and an embolization material are administrated together to maintain the anticancer drug concentration in the tumor high, are known. On the other hand, by development of catheter and its operation method, it has become possible to carry the microparticle carrier or embolization material to a specific site selectively and precisely.

As embolization materials, so far a gelatin sponge, polyvinyl alcohol, a degradable starch particle (DSM), an iodine addition products obtained from poppy seed oil, a crosslinked collagen fiber, an ethyl cellulose microcapsule, cyanoacrylate, stainless coil, etc., have been used. Among them, embolization material consisting of polymer particle can be, in a dispersed state in such as contrast agent, introduced into the body by injecting to an affected region by such as microsyringe via a microcatheter arranged in the body. Such embolization material of polymer particle can form an embolization by arriving at an affected region located in a deep portion.

However, there are following problems in the microparticle carrier consisting of polymer particle or the embolization material.

(1) Since its shape is irregular and particle size distribution is wide, there may be cases where its function cannot be exhibited at desired portion.

(2) In a tube of pharmaceutical and medical application devices such as catheter, needle or syringe, it may aggregate or its viscosity may increase to clog the tube. In particular, the clogging frequently occurs when a particle smaller than inner diameter of the catheter is passed through.

(3) It may not be able to be carried to a desired site since it aggregates or its viscosity increases in a normal blood vessel on the way to an affected region.

(4) In case where it is used as an embolization material, since its material quality is hard and does not fit to cross-sectional shape of a blood vessel, although it may decrease blood flow, it may not be able to perfectly embolize.

(5) Furthermore, as a degradable material in vivo, depending on a slight difference of environment where it is placed, such as whether it is a site contacting with blood or not, its degrading rate may change greatly.

(6) Since particle diameter is not appropriate, it may not be able to be indwelled at a desired site.

(7) In particular, in case of a particle which is smaller than inner diameter of the catheter, after passing through the catheter, since it is carried to an affected region in a crushed condition without recovering to its original shape, it may embolize at a farther site than desired.

As prior arts, particles consisting of polylactic acid (hereafter, referred to as PLA) or poly (lactic acid/glycolic acid) copolymer (hereafter, referred to as PLGA) which are biodegradable polymers (refer to Nonpatent reference 1), or a biodegradable material containing a specified agent are disclosed (refer to Patent reference 3), but since hydrophobicity of the these substrates are high, and there were problems of the above-mentioned (2) to (5).

On the other hand, an application to drug manufacturing or to veterinary drug of a technique in which a drug is mixed to a substrate polymer consisting of a structure such as PLA-PEG, PLA-PEG-PLA or PLGA-PEG-PLGA, as a block copolymer consisting of polyethylene glycol (hereafter, referred to as PEG) and PLA or PLGA, to sustain release the drug, is disclosed (refer to Patent reference 4). However, in this technique, it was impossible to control softness and necessary strength for molding of the substrate polymer, and there were problems in at least one of the above-mentioned (1) to (5).

Furthermore, an embolization material consisting of a water insoluble PEG-based copolymer is disclosed (Patent reference 5). However, in this case, too, it was impossible to control softness and necessary strength for molding of the substrate polymer, and there were problems in at least one of the above-mentioned (1) to (5) and (7).

As a technique for improving clogging in catheter tube when the above-mentioned biodegradable particle is carried by an injection from the catheter, a particle consisting of water insoluble polymer such as polyethylene glycol-based copolymer of which film tensile modulus is 1500 MPa or less, is disclosed (Patent reference 6). However, the technique disclosed here is, as indicated in the examples of the reference, nothing more than a technique of improving passing ability through catheter of a particle size smaller than inner diameter of the catheter tube, and since it is not an invention of improving passing ability of a particle of which diameter is larger than inner diameter of the catheter tube, a molecular weight range, composition or the like of the copolymer necessary for preventing clogging in the catheter tube of a particle having a diameter larger than inner diameter of the catheter tube, has not been found.

Furthermore, in Patent references 5 and 6, no reference is made about the problem (7) which relates to a recovery after passing catheter, i.e., molecular weight range, composition or the like of the copolymer necessary for the recovery, has not been found.

[Patent reference 1] JP-3242118C
[Patent reference 2] JP-3428972C
[Patent reference 3] JP-H5-969A
[Patent reference 4] JP-H5-17245B
[Patent reference 5] JP2004-167229A
[Patent reference 6] JP2004-313759A
[Nonpatent reference 1] Bastian P, Bartkowski R et al., Chemo-embolization of experimental liver metastases, European Journal of Pharmaceutics and Biopharmaceutics, 1998, vol. 43, p 243-254.

DISCLOSURE OF THE INVENTION

Problem to be Solved by the Invention

The object of the present invention is to provide a biodegradable particle capable of not clogging by an aggregation in a micro diameter tube such as of a catheter, needle or syringe mainly used in pharmaceutical and medical applications or in a blood vessel, and capable of recovering to original shape after passing the tube, and capable of being smoothly degraded after passing a specified period of time so that degraded component can finally be absorbed or discharged in vitro.

Means for Solving the Problem

1. A biodegradable particle characterized in that a compressive modulus of the particle in water saturated state is 10 MPa or less.
2. A biodegradable particle containing a water-soluble polymer and a biodegradable polymer characterized in having a substrate of which containing ratio of said water-soluble polymer with respect to said biodegradable polymer is 0.60 to 0.70.
3. A biodegradable particle described in the above item 2 characterized in having a degradability in 37° C. phosphate buffered saline.
4. A biodegradable particle described in the above item 2 or 3 characterized in that its average particle diameter is 100 μm or more and, in water saturated state, a particle diameter after passing through a catheter having an inner diameter of 60% or more and 85% or less of said particle diameter is larger than the inner diameter of said catheter.
5. A biodegradable particle described in any one of the above items 2 to 4 characterized in that a compressive modulus of the particle in water saturated state is 10 MPa or less.
6. A biodegradable particle described in any one of the above items 1 to 5 characterized in that said water-soluble polymer is a polyalkylene glycol or a derivative thereof.
7. A biodegradable particle described in the above item 6 characterized in that a weight average molecular weight of said polyalkylene glycol is 200 or more and 40,000 or less.
8. A biodegradable particle characterized in being a particle of which particle diameter is 5 μm or more and coated with a polyalkylene glycol or a derivative thereof.
9. A biodegradable particle described in any one of the above items 1 to 7 characterized in being coated with a polyalkylene glycol or a derivative thereof.
10. A biodegradable particle described in any one of the above item 8 or 9 characterized in that a weight average molecular weight of said polyalkylene glycol is 1,000 or more and 40,000 or less.
11. A biodegradable particle described in any one of the above items 6 to 10 characterized in that said polyalkylene glycol is a polyethylene glycol.
12. A biodegradable particle described in any one of the above items 1 to 11 characterized in that a particle diameter is 5 to 2000 μm.
13. A biodegradable particle described in any one of the above items 1 to 12 characterized in that a particle size distribution is within ±60% of its average particle diameter.
14. A biodegradable particle described in any one of the above item 12 or 13 characterized in that the particle is spherical.
15. A biodegradable particle described in any one of the above items 2 to 14 characterized in that said biodegradable polymer contains α-hydroxy acid unit.
16. A biodegradable particle described in any one of the above items 2 to 15 characterized in that a weight average molecular weight of water insoluble copolymer comprising said water-soluble polymer and said biodegradable polymer is 1,000 to 100,000.
17. A biodegradable particle described in any one of the above items 1 to 16 characterized in being used in pharmaceutical and medical applications.
18. A biodegradable particle described in any one of the above items 1 to 16 characterized in being used as an indwelling device.
19. A biodegradable particle described in the above item 18 characterized in being used for embolization therapy.
20. A production method of biodegradable particle characterized in that the particle is obtained by blending a water insoluble polymer A of which film has a tensile modulus of 1 MPa or more and less than 50 MPa in water saturated state and a water insoluble polymer B of which film has a tensile modulus of 50 MPa or more in water saturated state.
21. A production method of biodegradable particle described in the above item 20 characterized in that a blend ratio of said water insoluble polymer B is 20 wt % or more.
22. A production method of a biodegradable particle obtainable from a water-soluble polymer and a biodegradable polymer characterized in that it is a production method of a biodegradable particle by blending a water insoluble polymer C of which weight ratio of the water-soluble polymer is 50% or more and a water insoluble polymer D of which weight ratio of the water-soluble polymer is less than 50%.
23. A production method of biodegradable particle described in the above item 22 characterized in that a blend ratio of said water insoluble polymer D is 20 wt % or more.
24. A production method of biodegradable particle described in any one of the above items 20 to 23 characterized in that said water insoluble polymer is a copolymer in which the water-soluble polymer and the biodegradable polymer is chemically bonded.
25. A biodegradable particle described in the above item 1 or 19 characterized by being made by the production method of biodegradable particle described in any one of the above items 20 to 24.

Effect of the Invention

According to the present invention, as explained in the following, it is possible to provide a particle capable of not clogging by an aggregation in a micro diameter tube of devices such as a catheter, needle or syringe mainly used in pharmaceutical and medical applications or in a blood vessel and capable of recovering to original shape after passing the tube, and furthermore, not depending on indwelled site or indwelled environment, capable of being smoothly degraded after passing a specified period of time so that degraded component can finally be absorbed or discharged in vitro.

BEST EMBODIMENT FOR CARRYING OUT THE INVENTION

The biodegradable particle of the present invention is a particle degradable by a chemical decomposition represented by hydrolysis or by an enzyme produced by a cell or a microorganism. Mainly, a hydrolyzable one is preferable. As starting materials used for the biodegradable particle, it is not especially limited, but may be any one of a natural polymers or an artificially synthesized polymers, and polyesters, polyethers, polyacid anhydrides, polypeptides, poly (α-cyanoacrylate)s polyacrylamides, poly (ortho esters), polyphosphazenes, polyamino acids, biodegradable polyurethanes, polycarbonates, polyiminocarbonates, nucleic acids, polysaccharides or the like are mentioned, and as concrete representative examples, gelatin, chitin, chitosan, dextran, gum ababic, alginic acid, starch, polylactic acid (hereafter, referred to as PLA), polyglycolic acid (hereafter, referred to as PGA), polylactic acid glycolic acid copolymer (hereafter, referred to as PLGA), hydroxy terminal poly (ε-caprolactone)-polyether, polycaprolactone, n-butyl cyanoacrylate, copolymer consisting of the above-mentioned polymer, etc., are mentioned.

As the first embodiment of the biodegradable particle of the present invention, since it is preferable that a material having an elasticity capable of passing through a micro diameter tube smaller than the particle size and capable of keeping a necessary strength in catheter tube or in blood vessel, etc., it is good that a compressive modulus in water saturated state is 10 MPa or less, to be 0.5 MPa or more and 10 MPa or less is preferable, to be 5 MPa or less is more preferable and to be 3 MPa or less is still more preferable. The water saturated state mentioned here means a state in which water content becomes constant for a material immersed in pure water of ordinary temperature. Whereas, to be constant in water content means, for a specified material, to be within 3% in weight change in several hours. A material having a compressive modulus exceeding 10 MPa in water saturated state is hard and not suitable as a material which is administrated by such as a microcatheter having a smaller tube than the particle diameter of the biodegradable particle.

The modulus characteristics are, for example, can be evaluated as follows.

[Measuring Condition]
Compression tester: MCT-W500; Shimadzu Corp. (or, may be an instrument by which same result in same condition can be obtained.)
Test room temperature 25° C.
Test room humidity: 50%
Upper indenter: flat type ϕ500 μm
Load speed: 4.462 mN/sec Based on a stress-strain curve obtained by this way, compressive modulus was determined by using the following equation.

$$\text{Compressive modulus (unit: MPa)} = (\delta 2 - \delta 1)/(\epsilon 2 - \epsilon 1)$$

Here, strain $\epsilon 1 = 0.0005$, strain $\epsilon = 0.0025$. $\delta 1$ and $\delta 2$ are compressive stresses corresponding to $\epsilon 1$ and $\epsilon 2$ which can be determined based simply on the stress-strain curve.

In the present invention, in order to exhibit a soft elasticity so that it can easily pass through micro diameter tube, it is preferable to blend at least 2 kinds of water insoluble polymer different in tensile modulus. In concrete, it is preferable that the water insoluble polymer constituting the particle has film forming ability, and one polymer (polymer A) which forms the water insoluble polymer has a film tensile modulus of 1 MPa or more and less than 50 MPa in water saturated state and another polymer (polymer B) is 50 MPa or more and 400 MPa or less. Furthermore, in order to maintain necessary strength, it is most preferable that a ratio of polymer B is 20 wt % or more. Modulus of the particle obtained by such blend cannot be obtained by controlling composition of single polymer component.

The film tensile modulus of the present invention is one of tensile characteristics of film, but the film tensile characteristics in water saturated state of the present invention mean characteristics such as modulus or elongation obtained by measuring after immersing the film obtained from the water insoluble polymer having film forming ability in pure water at normal temperature until its water content ratio becomes constant. Whereas, to be constant in water content means, for a specified material, to be within 3% in weight change even after several hours.

The film tensile characteristics can be evaluated, for example, according to the following way, or may be evaluated in a method in which same result can be obtained. Whereas, as film forming methods, there are casting method, bar coater method, etc., but the tensile modulus of the present invention is a value measured for a film formed by casting method.

[Measuring Condition]
Tensile tester: RTM-100 model; produced by Orientec Corporation (or, may be an instrument by which same result can be obtained.)
Test room temperature: 25° C.
Test room humidity: 50%
Test piece shape: narrow card-shaped (80 mm×7.5 mm)
Test piece thickness: 30 μm±10 μm
Chuck-to-chuck distance: 20 mm
Test speed: 10 mm/min Whereas, to the biodegradable particle of the present invention, in addition to the above-mentioned at least 2 kinds of polymer of which tensile moduli are different, other component mentioned later, i.e., oily contrast medium, pharmaceutically effective component, etc., may be added.

Shape of biodegradable particle of the present invention is not especially limited, but in case where pharmaceutical and medical applications to human body are especially considered, it is preferable that a particle shape is maintained at 37° C., and furthermore, a spherical particle is preferable. The spherical particle mentioned here means a particle, when the particle is observed from an arbitrary direction as a circle, of which ratio of length perpendicular to maximum length with respect to the maximum inner diameter length of the circle is in the range of 0.5 or more and 1.0 or less, preferably 0.8 or more and 1.0 or less, i.e., not only perfect spherical shape, but also an ellipsoid or a rotational ellipsoid such as rugby ball type are also included. And, in case where particle of the present invention does not maintain particle shape at 37° C., e.g., a liquid state or a gel state, it may not be indwelled in a desired site due to its low strength. On the other hand, in case of a particle of which spherical shape is maintained, it becomes possible to more effectively be indwelled or exhibit aimed functions.

It is preferable that the biodegradable particle of the present invention has degradability in 37° C. phosphate buffered saline, and since it has such characteristics, it becomes possible to use it for pharmaceutical and medical applications, especially for embolization material application to be indwelled.

In the present invention, to have degradability in 37° C. phosphate buffered saline means that dried weight of particle or weight average molecular weight of polymer constituting the particle after immersion in 37° C. phosphate buffered saline for a predetermined term decreases 80% or less of those before the immersion. The term for the immersion is not especially limited and there may be a polymer degradable after passing a long period of time.

Furthermore, as characteristics of the second embodiment of the biodegradable particle of the present invention, it is preferable that, in case of average particle diameter is 100 µm or more and in water saturated state, after passing, without resistance, through a micro diameter tube of which inner diameter is smaller than the particle size, the above-mentioned preferable spherical shape (spherical), i.e., "a shape in which ratio of length perpendicular to maximum length with respect to maximum inner diameter length of the circle is included in the range of 0.8 or more and 1.0 or less" is maintained. In particular, it is preferable that the sphericity is maintained after passing through micro diameter tube of which inner diameter size is 60% or more and 85% or less with respect to the particle diameter. At passing through such micro diameter tube, biodegradable particle deforms in a direction of being compressed, to an extent of 15% or more and 40% or less of the particle diameter. Accordingly, the biodegradable particle of the present invention has characteristic, in case where it is deformed by a compressive load, of recovering to spherical when the load is removed, and it is preferable to recover to original shape. In particular, in case where it is used for embolization material application, since catheter is thinner than a blood vessel to be embolized, particle must have a shape capable of embolizing the blood vessel just after passing through the catheter. Accordingly, in case of the biodegradable particle in water saturated state, when such biodegradable particle is passed through a catheter having an inner diameter of 60% or more and 85% or less of the particle diameter, it is preferable that, even no external operation is added, the particle diameter of the biodegradable particle after passing through automatically becomes the inner diameter of the catheter or more.

Whereas, the water saturated state mentioned here means a state in which weight change of water content ratio of a material immersed in pure water of normal temperature for several hours becomes 3% or less.

That is, for example, in case where it is used for an embolization of blood vessel, particle, which is administrated into blood vessel by using microcatheter or the like, which cannot maintain sphericity in a water saturated state with water component in blood is inappropriate because a possibility to embolize a site farther than a predetermined site is very high since its particle diameter becomes small in specified direction.

Constitution of the second embodiment of the biodegradable particle of the present invention contains a water-soluble polymer and a biodegradable polymer, and has a substrate of which containing ratio of the water-soluble polymer with respect to said biodegradable polymer is 0.60 to 0.70. In case where a containing ratio of the water-soluble polymer with respect to said biodegradable polymer is less than 0.60, its softness is insufficient especially when it is molded into a particle, and a particle of its diameter is larger than the inner diameter of catheter cannot pass through the catheter. And, in case where it is more than 0.70, its shape does not recover after passing through catheter, i.e., a recoverability is not maintained. Contents of the water-soluble polymer and the biodegradable polymer can be known by measuring $^1$H-NMR. In concrete, it can be determined by integral value of signals of the chemical shifts of proton characteristic to the water-soluble polymer and the biodegradable polymer, respectively, i.e., number of hydrogen atoms contained in repeating unit and molecular weight of the repeating unit. For example, in case of a water insoluble copolymer comprising polyethylene glycol and poly (lactic acid-glycolic acid) copolymer, provided that a relative integral value of signals of chemical shift 3.4-3.7 ppm based on 4 hydrogen atoms of ethylene group of polyethylene glycol is A, a relative integral value of signals of chemical shift 1.4-1.6 ppm based on 3 hydrogen atoms of methyl group of lactic acid unit is B, and a relative integral value of signals of chemical shift 4.7-4.9 ppm based on 2 hydrogen atoms of methylene group of glycolic acid unit is C, a content of polyethylene glycol is expressed by the following equation by using the molecular weights 44, 72 and 58 of the respective repeating units.

$$\text{Content (\%)}=100\times(44\times A/4)/((44\times A/4)+(72\times B/3)+(58\times C/2))$$

Furthermore, in particle of such embodiment of the present invention, it is preferable that a compressive modulus is 10 MPa or less, and in order to exhibit such characteristic, it is preferable to blend at least 2 kinds of water insoluble polymer A and polymer B of which tensile modulus are different.

As granulation method of particle, known methods such as tumbling granulation method, fluidized bed granulation method, spray layer granulation method, agitation granulation method, crush granulation method, compression granulation method, extrusion granulation method or drop solidification granulation method can be employed. For example, in the drop solidification granulation method, a water insoluble polymer is dissolved in dichloromethane, chloroform, ethyl acetate or isopropyl ether, etc., and this solution is dispersed in a water phase containing a surface active agent, protective colloid agent or the like, and it can be made into a particulate state by known oil/water type (hereafter, referred to as O/W type) or water/oil/water type (hereafter, referred to as W/O/W type) drying-in-liquid method or other similar methods, spray dry method or the like to produce a particle. Surface active agent or protective colloid agent used here is not especially limited, as far as it can form a stable O/W type emulsion, but for example, anionic surface active agents (sodium oleate, sodium stearate, sodium lauryl sulfate, etc.), nonionic surface active agents (polyoxyethylene sorbitan fatty acid ester, polyoxyethylene sorbitan castor oil derivatives, etc.), polyvinyl alcohol, polyvinyl pyrrolidone, carboxymethyl cellulose, lecithin, gelatin or the like are mentioned. From these, one kind or a plural of them in combination may be used. In particular, polyvinyl alcohol, carboxymethyl cellulose and gelatin are preferable. Concentration of said aqueous solution is selected from 0.01 to 80 wt %, and more preferably, selected from 0.05 to 60 wt %, and by controlling this concentration, particle shape and/or particle diameter can be controlled. And, by controlling polymer concentration of the water insoluble polymer solution, too, particle shape and particle diameter become easy to be controlled. Particle made by the above-mentioned production method is generally a spherical particle, but contains particles of various particle diameters. In order to obtain a particle of desired particle diameter or desired particle size distribution, a plural of sieves can be used. A plural of sieves are piled in the order of fineness of its opening, and the particle dispersed liquid prepared by the above-mentioned production method is poured into the uppermost sieve of which opening is the largest, and the particle can be fractionated into respective particle diameters since particle stays on a sieve of which mesh size is smaller than the particle diameter. The mesh size of sieve is not especially limited, and it may appropriately be selected according to desired particle diameter and particle size distribution.

It is preferable that particle diameter of the biodegradable particle of the present invention is 5 to 2,000 µm, and further, it is preferable to be 10 to 1,500 µm. In case where the biodegradable particle is used as a microparticle carrier, when the particle diameter is in this range, it is preferable since the particle can be indwelled smoothly via a catheter, needle, syringe or the like, to enable to exhibit its function in an aimed site. And, in case where the biodegradable particle is used for embolization, when the particle diameter is in this range, it is preferable since this range enables to effectively embolize an aimed site. And, when it is used for such uses, the particle size distribution is ±60% or less of the average particle diameter, further, it is more preferable to be ±50% or less of the average particle diameter.

In the present invention, the particle diameter, the average particle diameter and the particle size distribution means those in pure water or physiological saline solution at 25° C. The measurement of the average particle diameter and particle size distribution of particle of the present invention is possible by various commercially available measurement instruments, especially, particle size distribution analyzer "MICROTRAC series" produced by Leeds and Northrup Co. is preferable since a measurement can be carried out in physiological saline solution, i.e., can be measured in a condition close to blood vessel or environment in vivo. And, it is no problem if it is an instrument by which an equivalent result can be obtained. The average particle diameter is calculated as volume average value and in "MICROTRAC series", it is expressed as "MV" value without depending on sphericity of particle.

It is preferable that the water insoluble polymer of the present invention comprises a copolymer in which the water-soluble polymer and the biodegradable polymer are chemically bonded. The water-soluble polymer mentioned in the present invention is a polymer which dissolves completely to give a uniform solution when the polymer is added to water at normal pressure and in saturated concentration or less. Time and temperature necessary to dissolve the polymer are not especially limited. And, water insoluble polymer means a polymer which does not meet the definition of such water-soluble polymer. By controlling ratio of the water-soluble polymer and the biodegradable polymer in such copolymer, the water insoluble polymer A and the water insoluble polymer B above-mentioned can be respectively prepared, and by blending these, the biodegradable particle of the present invention can be obtained. A concrete ratio is not especially limited, but it is preferable to blend water insoluble polymer C of which weight ratio of water-soluble polymer in the water insoluble polymer is 50% or more and water insoluble copolymer D of which weight ratio of water-soluble polymer is less than 50%. Furthermore, in order to maintain necessary strength, it is most preferable that the ratio of polymer D is 20 wt % or more.

Furthermore, as such water-soluble polymer, those comprising polyalkylene glycol are preferable. The water insoluble copolymers in which such water-soluble polymer is used, that is, water insoluble polyalkylene glycol-based copolymer is a block copolymer or the like of which one component is polyalkylene glycol or its derivative. It may be those insolubilized by a physical interaction with the polyalkylene glycol or its derivative. As the polyalkylene glycols, polyethylene glycol (hereafter, referred to as PEG) and polypropylene glycol are mentioned, but PEG is most preferable since it has biocompatibility and there are achievements in pharmaceutical and medical applications. In particular, it is preferable to comprise a water insoluble PEG-based copolymer in which PEG or PEG derivative and a biodegradable polymer are chemically bonded and, although it is not especially limited, a copolymer in which a biodegradable polymer is bonded to both or one terminal of PEG or a copolymer in which PEG and a biodegradable polymer are bonded alternatively are preferably used.

Furthermore, the biodegradable polymer mentioned here means a polymer which decomposes by a chemical decomposition represented by hydrolysis or by an enzyme produced by a cell or a microorganism. Kind of such biodegradable polymer is not especially limited and polyesters, polysaccharides, polypeptides or the like are preferable, but those containing α-hydroxy acid unit is most preferable. As examples containing α-hydroxy acid unit, polylactic acid and polyglycolic acid are mentioned. As starting material of such biodegradable polymer which is a biodegradable polymer having a property to chemically bond with PEG or PEG derivative, although it is not especially limited, lactic acid, glycolic acid, 2-hydroxybutylic acid, 2-hydroxyvaleric acid, 2-hydroxycaproic acid, 2-hydroxycapric acid, lactide, glycolide, malic acid, etc., can be mentioned, and it is preferable to contain any one or more of them, further, it is more preferable to use 2 kinds or more in combination to copolymerize, especially, the combination of lactic acid (or lactide) and glycolic acid (or glycolide) is preferable. In this case, it is preferable that weight ratio of lactic acid and glycolic acid is 100:0 to 30:70. Whereas, in the above-mentioned, in case of a compound having an optical activity in molecule such as lactic acid or lactide, it may be any one of D isomer, L isomer, DL isomer or a mixture of D isomer and L isomer.

It is preferable that the biodegradable particle of the present invention contains a water insoluble copolymer of which weight average molecular weight is 1,000 to 100,000, preferably 2,000 to 90,000, for example, a water insoluble polyalkylene glycol-based copolymer, in its core portion. When the weight average molecular weight is less than 1,000, it becomes into a gel state and sticks to tube surface of catheter or needle and may not arrive at an aimed site, on the other hand, when the weight average molecular weight exceeds 100,000, term for degrading the particle in vivo may become too long.

Furthermore, it is preferable that the weight average molecular weight of such polyalkylene glycol or its derivative is 200 to 40,000. If it is smaller than 200, hydrophilicity of the polyalkylene glycol-based copolymer is low and a uniform biodegradability may not be obtained. On the other hand, if it is larger than 40,000, polyalkylene glycol produced from degraded copolymer in vivo may become difficult to be discharged in vitro. And, structure of polyalkylene glycol derivative is not especially limited, and a structure including multi-armed polyalkylene glycol derivative can be preferably used. Weight ratio of the polyalkylene glycol or its derivative and the biodegradable polymer is not especially limited, but it can be more preferably used in the range of 80:20 to 5:95.

Hereafter, as a representative example of production method of the water insoluble polymer of the present invention, a production method of water insoluble polyalkylene glycol-based copolymer comprising polyalkylene glycol or polyalkylene glycol derivative and biodegradable polymer is exemplified. Methods for synthesizing the water insoluble polyalkylene glycol-based copolymer are not especially limited, but melt polymerization, ring-opening polymerization or the like are mentioned. For example, in dried air or in nitrogen flow, as starting material, a water-soluble polymer (polyalkylene glycol or polyalkylene glycol derivative) of a predetermined average molecular weight and a starting material of biodegradable polymer (monomer, etc.) are fed into a polymerization vessel equipped with a stirrer, and by heating the mixture while stirring with a catalyst, a water insoluble copolymer can be obtained. The catalyst used is not especially limited as far as it is a catalyst used in ordinary polymerization of polyester. For example, halogenated tin such as tin chloride, organic acid tin salts such as tin 2-ethyl hexanoate, organic alkali metal compounds such as diethyl zinc, zinc lactate, iron lactate, dimethyl aluminum, calcium hydride, butyl lithium, potassium t-butoxide or the like, metal alkoxides such as metalloporphyrin complex, diethyl aluminum methoxide or the like can be mentioned. And, it is also possible to carry out a polymerization by using a twin screw kneading/extruding machine equipped with a vent or a similar machine with stirring and extruding function, and by taking out water insoluble polymer continuously produced by stirring, mixing and degassing starting material of the biodegradable polymer, polyalkylene glycol or polyalkylene glycol derivative and catalyst, in molten state. Furthermore, it is possible to improve fractionation precision by a reprecipitation operation in which the produced water insoluble polymer is dissolved in a good solvent and a poor solvent is dropped to this to produce a precipitate and then after dissolving the precipitate by changing temperature of cloudy substance, slowly returning to original temperature to regenerate the precipitate. As the good solvent to be used in the above-mentioned fractionation precipitation, for example, tetrahydrofuran, a halogen-based organic solvent (dichloromethane, chloroform) or a mixed solvent thereof can be exemplified. As the poor solvent to be used in the above-mentioned fractionation precipitation, alcohol-based or hydrocarbon-based organic solvent is preferable. And, by selecting kind of biodegradable polymer and water-soluble polymer, furthermore, by appropriately selecting their molecular weight, various kinds of water insoluble polyalkylene glycol-based copolymer can be produced.

In the above-mentioned, although water insoluble polyalkylene glycol-based copolymer is exemplified, instead of using polyalkylene glycol, by using polyhydroxymethyl acrylate, acrylic acid, methacrylic acid, polyvinyl pyrrolidone or the like, too, it is possible to similarly obtain the water insoluble polymer.

The $3^{rd}$ embodiment of biodegradable particle in the present invention is a particle of which particle diameter is 5 µm or more and characterized by being coated with polyalkylene glycol or its derivative.

By coating surface of the biodegradable particle with a hydrophilic synthetic polymer, it becomes possible to impart lubricancy to the particle. Here, the hydrophilic synthetic polymer of the present invention means a synthetic polymer which swells in water or which is water-soluble. In case where it is indwelled or administrated, since it is preferable to be dissolved in body fluid, a water-soluble synthetic polymer is preferable, and polyalkylene glycol or its derivative such as polyethylene glycol, polypropylene glycol, and polyhydroxymethyl acrylate, acrylic acid, methacrylic acid, polyvinyl pyrrolidone or the like are mentioned as examples, but in the present invention, in view of moldability without aggregation or cohesion between particles, polyalkylene glycol or its derivative is used. In particular, in view of achievements in clinical practice and high biocompatibility, polyethylene glycol (hereafter, referred to as PEG) is most preferable. And, as an embodiment of the coating of the present invention, a state in which a hydrophilic synthetic polymer is absorbed, to an extent such that the particle surface is modified, is mentioned, but it is not especially limited as far as it is an extent that a lubricancy is imparted to the particle surface by the hydrophilic synthetic polymer, and a state in which the particle is wrapped by polyalkylene glycol or even a state in which polyalkylene glycol is deposited partially are preferable. However, in order to impart lubricancy more firmly, it is preferable that the hydrophilic synthetic polymer is deposited on 30% or more, more preferably 40% or more of the surface area of the particle surface. As coating method on the particle surface, mechanical coating method, wet coating method, spray drying method, sugar coating method, powder coating method or the like are mentioned. Among them, wet coating method and spray drying method are preferably used. In particular, a method of contacting the particle with the coating solution by agitating the particle in the coating solution, or a wet coating in which the particle is contacted with the coating solution by placing the particle on a filter or on a sieve and by pouring the coating solution thereon and rinsed are most preferably employed since it is easy to control an absorbed amount of the hydrophilic synthetic polymer. Molecular weight of such polyalkylene glycol or its derivative is not especially limited as far as it is an extent to be able to be absorbed such that the surface can be modified, but when the molecular weight is less than 1,000, since it has a property to become a liquid at normal temperature in a low molecular weight, the particle surface may become to a liquid state and its handling becomes difficult. And, in pharmaceutical and medical applications, especially, in case where it is used by injecting or administrating in vivo, when the molecular weight is large, since it may not be discharged by glomerulus of kidney, it is preferable to use a polyalkylene glycol or its derivative of its average molecular weight is 40,000 or less. Accordingly, it is most preferable that the range of weight average molecular weight is 1,000 to 40,000.

As wet coating methods, melting method or solvent dilution method are preferably employed. Solvent used in the solvent dilution method is not especially limited as far as it uniformly dissolves a polymer to be coated and capable of being finally removed, but water, alcohols such as methanol, ketones such as acetone or halogenated compounds such as dichloromethane are mentioned. In particular, water is preferably used since not only it is economical but also its safety is high.

Concentration of the PEG solution at the wet coating is not especially limited as far as it is possible to uniformly dissolve the PEG, but when the concentration is too low, surface performance is not improved and a clogging may occur in narrow tube, and when it is too high, particle's viscosity becomes high and processability may become worse. Accordingly, the range of 1 wt % to 50 wt % is most preferable.

After subjecting to the wet coating in which the particle is contacted with the coating solution, by drying the particle, the biodegradable particle of the present invention can be obtained.

Since it is desired that the biodegradable particle of the present invention degrades in vivo after passing a predetermined period of time and the degraded component is a material which is absorbed or discharged in vitro, it is preferable to have a characteristic that a residual weight after immersion in 37° C. phosphate buffered saline (hereafter, abbreviated as PBS) for 28 days is 80% or less of the weight before the immersion. That is, since molecular weight of the biodegradable particle decreases due to its decomposition and becomes to easily dissolve in 37° C. PBS, it becomes possible to evaluate biodegradability by such a parameter. Whereas, the weight mentioned here means a weight of the particle in dried state. Furthermore, it is preferable that said residual weight is 70% or less, and 60% or less is more preferable.

Measurement of the weight after immersion in PBS for 28 days is not especially limited, but for example, it can be measured by the following method.

(Weight Measurement after Immersion in PBS for 28 Days)

Particle 20 mg (weight in dried state) is precisely weighed and put into a sterilized round bottom 10 ml spitz tube produced by Eikenkizai Co., and 10 ml of PBS (produced by Nacalai Tesque, concentrated 10 times, pH7.4, Code. No. 27575-31) diluted 10 times with pure water is injected. This is subjected to incubation in a thermostatic bath "Laboster LC-110" (produced by Tabai Espec Corp.) adjusted to 37° C. while being stirred by "Tube Rotertor TR-350" (produced by Iuch Seieido Co) of 100 rpm. The incubated solution is centrifuged at 3000 rpm and the supernatant is separated and replaced with a new PBS in every 7 days.

The particle after the immersion in PBS for 28 days is centrifuged at 3000 rpm and then the supernatant was removed, and furthermore it is washed with 10 ml pure water, and after centrifuged again at 3000 rpm to remove the pure water, it is vacuum dried until the particle weight becomes constant, and weight of the obtained particle is precisely weighed. Whereas, "particle weight becomes constant" mentioned here means a state in which a weight change after passing several hours is within 5%. Residual weight ratio (W) can be calculated from weight ($W_0$ (g)) before immersion in PBS and weight ($W_1$ (g)) after immersion for 28 days, by $W=W_1/W_0 \times 100$.

It is preferable that the biodegradable particle of the present invention has characteristic that its weight average molecular weight after immersion in 37° C. PBS for 28 days is 80% or less of the molecular weight before the immersion. Further, it is preferable that said weight average molecular weight is 70% or less, and 60% or less is more preferable. By having the characteristic that the weight average molecular weight after immersion in 37° C. PBS for 28 days is 80% or less, since changing to low molecular weight, dissolving or crushing of the particle material are smoothly carried out in vivo, volume occupied in vivo by the particle which is used and has become unnecessary decreases, and its influence to human body decreases.

Measuring method of the molecular weight is not especially limited, but for example, it can be measured by the following method.

(Measurement of Weight Average Molecular Weight)

Precisely weighed 10 mg particle is dissolved in 2 ml chloroform, and filtered by a filter for gel permeation chromatography (hereafter, abbreviated as GPC) "Millex LG13" (MILLIPORE SLLGH13NL). The filtrate is analyzed under the condition of 2 GPC columns (TSK-gel-GMH$_{HR}$-M of Tosoh Corp.), column temperature 35° C., mobile phase chloroform 1 ml/min, sample injection amount 100 µl and detect by a differential refractometer (RI-8010 produced by Tosoh Corp.). Calibration of the column is carried out with standard polystyrene of Tosoh Corp. just before the measurement.

Whereas, average molecular weight is calculated by work station for data analysis (Shimadzu Corp. "Class-Vp"), based on calibration curve obtained from the relation between molecular weight of standard polystyrene and column elution time.

The ratio of weight average molecular weight after immersion in PBS for 28 days to the molecular weight before the immersion (M (%)) can be calculated by M (%)=$M_1/M_0 \times 100$, from the weight average molecular weight before immersion in PBS ($M_0$) and the weight average molecular weight after immersion for 28 days ($M_1$).

It is more preferable that the biodegradable particle of the present invention satisfies both requirements that the residual weight after immersion in PBS for 28 days is 80% or less of the weight before the immersion, and the weight average molecular weight after immersion in PBS for 28 days is 80% or less of the molecular weight before the immersion. Method for controlling biodegradation rate is not especially limited, but by controlling molecular weight of the biodegradable polymer in the copolymer, that is, for example, by decreasing molecular weight of the biodegradable polymer to be chemically bonded by using multi-armed PEG derivative, or, by controlling crystallinity of the biodegradable polymer in the copolymer, that is, for example, by using PLGA as the biodegradable polymer, it is possible to more preferably control the biodegradation rate. And, it is preferable to make the core portion of the biodegradable particle to an internal dispersion type composite structure, or a coating type composite structure. It is possible to control biodegradation rate of the biodegradable particle by internally dispersing another water insoluble polymer into a water insoluble polymer, or by making these to a multi-layer, for example, by internally dispersing a water insoluble polymer having PLGA-PEG-PLGA structure into a water insoluble polymer having PLA-PEG-PLA structure.

Application of the biodegradable particle of the present invention is not especially limited, but especially, in pharmaceutical and medical applications in which catheter or needle are used and furthermore as a device to be indwelled, it is preferably used.

The device mentioned here means a device which has some function relating to therapy, diagnosis or prevention of diseases. Size, shape, material or structure of the device is not especially limited. For example, blood vessel embolization material, drug delivery system which slowly releases drug, etc., are mentioned.

The biodegradable particle of the present invention can be used as it is, or it can be used by being dispersed in an appropriate contrast medium or a dispersing medium. As contrast medium, water-soluble one is preferable, and known materials can be used, and it can be either of ionic or nonionic. In concrete, "Iopamiron" (produced by Schering AG), "Hexabrix" (Eiken Chemical Co.), "Omnipaque" (produced by Daiichi Pharmaceutical Co.), "Urografin" (produced by Schering AG), "Iomeron" (Produced by Eisai Co.), etc., can be mentioned. In this case, the particle and the contrast medium can also be injected to a predetermined site after being mixed beforehand. If the water content of the particle is high, it is preferable since the contrast medium is partly held inside the embolization material together with water, to efficiently exhibit the contrast effect. As examples of the dispersion medium, solutions with a dispersing agent (for example, polyoxysorbitan fatty acid ester, carboxymethyl cellulose, etc.), preservative (for example, methylparaben, propylparaben, etc.), or isotonic agent (for example, sodium chloride, mannitol, glucose, etc.) dispersed in distilled water for injection, and vegetable oils such as sesame oil or corn oil, are mentioned. When the dispersed particle is used by a catheter, it is administrated, via a catheter of which tip portion is introduced to a vicinity of desired site in vivo, while monitoring a position of the contrast medium from an adequate artery into a tumor-feeding artery by roentgenoscopy.

Furthermore, an antiseptic, stabilizer, isotonic agent, solubilizing agent, dispersing agent, excipient, etc. usually added to an injection can also be added to the embolizing agent.

The embolizing agent of this invention may also be used together with an oily contrast medium such as an iodine addition product obtained from poppy seed oil (Lipiodol Ultra-Fluid). And, it may also be used together with an iodine addition product obtained from poppy seed oil and an anticancer drug (for example, Smancs, neocarzinostatin, mitomycin-C, adriamycin, irinotecan hydrochloride, fluorouracil, epirubicin hydrochloride, cisplatin, paclitaxel, leucovorin calcium, vinblastine, Altretamine, bleomycin, Doxorubicin Hydrochloride, Picibanil, Krestin, lentinan, cyclophosphamide, thiotepa, tegafur, vinblastine sulfate, pirarubicin hydrochloride sulfate), etc.

The biodegradable particle of this invention can achieve the object of this invention, even if it does not contain a pharmaceutically effective component, but for the purpose of imparting a further effect, it is also preferable to contain a pharmaceutically effective component. The pharmaceutically effective component is not especially limited as far as its pharmaceutical effect is known, but as the pharmaceutically effective component, the above-mentioned anticancer drugs, vascularization inhibitors, steroid hormones, hepatic disease drugs, arthrifuges, antidiabetic agents, drugs for circulatory organs, hyperlipidemia drugs, bronchodilators, antiallergic drugs, drugs for digestive organs, antipsychotic drugs, chemical therapeutic agents, antioxidants, peptide-based drugs, protein-based drugs (for example, interferon), etc., are mentioned.

The biodegradable particle of the present invention can be used in various uses, but in view of high safety that it biodegrades and does not remain in vivo, it is most preferably used in pharmaceutical and medical fields. Among the pharmaceutical and medical applications, it is preferable to use as a carrier which carries drug or cell in vivo. And, it is most preferably used for so-called embolization therapy in which a tumor is attacked by starvation tactics by embolizing a blood vessel for supplying nutrition to the tumor.

EXAMPLES

The present invention is explained in more concretely by showing following experimental data of passing ability of the particle through a catheter, but the scope of the present invention is not limited to these examples. Measuring methods in the examples are shown in the followings.

(Average Particle Diameter and Particle Size Distribution)

By using particle size distribution analyzer "MICROTRAC series" produced by Leeds and Northrup Co., it was measured in physiological saline solution at 25° C. As the particle diameter, a value calculated as volume average denoted as "MV value" was employed.

(Compressive Modulus)

It was evaluated in the following condition by using MCT-W500 of Shimadzu Corp. as a compression tester.

Test room temperature: 25° C.
Test room humidity: 50%
Upper indentor: flat type φ500 μm
Loading rate: 4.462 mN/sec Based on a stress-strain curve obtained by this way, compressive modulus was determined by using the following equation.

$$\text{Compressive modulus (unit: MPa)} = (\delta 6 - \delta 1)/(\epsilon 2 - \epsilon 1)$$

Here, $\epsilon 1 = 0.0005$ and $\epsilon 2 = 0.0025$. $\delta 1$ and $\delta 2$ are compressive stresses corresponding to $\epsilon 1$ and $\epsilon 2$ which can be determined based simply on stress-strain curve.

(Tensile Modulus of Film)

Tensile modulus of film formed by cast method was evaluated by the following condition by using RTM-100 model produced by Orientec Corporation as a tensile tester.

Test room temperature: 25° C.
Test room humidity: 50%
Test piece shape: narrow card-shaped (80 mm×7.5 mm)
Test piece thickness: 30 μm±10 μm
Chuck-to-chuck distance: 20 mm
Test speed: 10 mm/min (Weight Measurement after Immersion in PBS for 28 Days)

Particle 20 mg (weight in dried state) was precisely weighed and put into a sterilized round bottom 10 ml spitz tube produced by Eikenkizai Co., and 10 ml of PBS (produced by Nacalai Tesque, concentrated 10 times, pH 7.4, Code No. 27575-31) diluted 10 times with pure water was injected. This was subjected to incubation in a thermostatic bath "Laboster LC-110" (produced by Tabai Espec Corp.) adjusted to 37° C. while being stirred by "Tube Rotertor TR-350" (produced by Iuch Seieido Co.) of 100 rpm. The incubated solution was centrifuged at 3000 rpm and the supernatant was separated and replaced with a new PBS in every 7 days.

The particle after the immersion in PBS for 28 days was centrifuged at 3000 rpm and then the supernatant was removed, and furthermore it was washed with 10 ml pure water, and after centrifuged again at 3000 rpm to remove the pure water, it was vacuum dried until the particle weight became constant, and weight of the obtained particle was precisely weighed. Residual weight ratio (W) can be calculated from weight ($W_0$ (g)) before immersion in PBS and weight ($W_1$ (g)) after immersion for 28 days, by $W = W_1/W_0 \times 100$.

(Measurement of Weight Average Molecular Weight)

Precisely weighed 10 mg particle was dissolved in 2 ml chloroform, and filtered by a filter for gel permeation chromatography (hereafter, abbreviated as GPC) "Millex LG13" (MILLIPORE SLLGH13NL). The filtrate was analyzed under the condition of 2 GPC columns (TSK-gel-GMH$_{HR}$-M of Tosoh Corp.), column temperature 35° C., mobile phase chloroform 1 ml/min, sample injection amount 100 μl and measured by a differential refractometer (RI-8010 produced by Tosoh Corp.). Calibration of the column was carried out with standard polystyrene of Tosoh Corp. just before the measurement.

Whereas, average molecular weight was calculated by work station for data analysis (Shimadzu Corp., "Class-Vp"), based on calibration curve obtained from the relation between molecular weight of standard polystyrene and column elution time.

(Calculation of Polyethylene Glycol Content)

Polymer 0.1 g was dissolved in 1 mL deuterium chloroform, and $^1$H-NMR was measured by 270 MHz super conductive FT-NMR EX-270 (produced by JOEL Co.).

Provided that, a relative integral value of signals of chemical shift 3.4-3.7 ppm based on 4 hydrogen atoms of ethylene group of polyethylene glycol is A, a relative integral value of signals of chemical shift 1.4-1.6 ppm based on 3 hydrogen atoms of methyl group of lactic acid unit is B, and a relative integral value of signals of chemical shift 4.7-4.9 ppm based on 2 hydrogen atoms of methylene group of glycolic acid unit is C, a content of polyethylene glycol is expressed by the following equation by using the molecular weights 44, 72 and 58 of the respective repeating units.

$$\text{Content (\%)} = 100 \times (44 \times A/4)/((44 \times A/4) + (72 \times B/3) + (58 \times C/2))$$

(Passing Ability Through Catheter)

In respective examples and comparative examples, evaluations were carried out by injecting the obtained particle dispersion from a syringe to a catheter, and a case where it was possible to inject with no resistance was taken as ○, and a case where there was resistance and an injection was impossible was taken as x. However, in Examples 4 to 6 and Comparative examples 2 to 5, a case where it was possible to inject with no resistance and particle maintained sphericity after passing through the catheter was taken as ○, a case where it was possible to inject with no resistance, but the particle did not maintain sphericity after passing through the catheter was taken as Δ, and a case where there was a big resistance and an injection was impossible was taken as x. Except stated otherwise, as the catheter, FasTRACKER-10 Infusion Catheter (catheter length is 155 cm, inner diameter of tip portion is 380 μm) produced by Boston Scientific Corp. was used.

Synthesis Example 1

Under nitrogen flow, L-lactide (produced by Purac Biochem Ltd.) 4.96 g, glycolide (produced by Boehringer Ingelheim Co.) 1.66 g and dehydrated PEG (Sunbright DKH-20T produced by Nihon Yushi Kogyo Co.) 2.88 g were mixed in a flask and after dissolved and mixed at 150° C., a toluene solution 460 μL in which tin dioctanoate (produced by Wako Pure Chemical Industries, Ltd.) was dissolved so that its concentration was 0.1 mol/L was added and reacted to thereby obtain a water insoluble polymer having PLGA-PEG-PLGA structure of which water-soluble polymer weight ratio is 30.3%. This water insoluble polymer was dissolved in chloroform and dropped into a greatly excessive amount of diethyl ether/acetone mixed liquid to obtain a white precipitate. Weight average molecular weight according to the above-mentioned GPC method was 22,000.

The obtained purified polymer was dissolved in dichloromethane so that its concentration was 30 wt %. Said solution was poured into a laboratory dish of inner diameter 85 mm and was left for one day and night at 20° C. to evaporate dichloromethane and obtained a film of 20 μm thickness. When this was immersed in pure water at room temperature, water content became constant in about 3 hours. When a tensile test was carried out under the water saturated state, tensile modulus of the film was 57 MPa.

Synthesis Example 2

Under nitrogen flow, L-lactide (produced by Purac Biochem Ltd.) 1.92 g, glycolide (produced by Boehringer Ingelheim Co.) 0.96 g and dehydrated PEG (Sunbright MEH-20T produced by Nihon Yushi Kogyo Co.) 2.88 g were mixed in a flask and dissolved, mixed and reacted in the same way as Synthesis example 1, to thereby obtain a water insoluble polymer having PLGA-PEG structure of which water-soluble polymer weight ratio is 50.0%. From this water insoluble polymer, a white precipitate was obtained in the same way as Synthesis example 1. Weight average molecular weight according to the above-mentioned GPC method was 14,000.

By using the obtained purified polymer, a film forming was carried out in the same way as Synthesis example 1, and obtained a film of 20 μm thickness. When this was immersed in pure water at room temperature, water content became constant in about 3 hours. When a tensile test was carried out under the wet condition, tensile modulus of the film was 2.1 MPa.

TABLE 1

| | L-lactide (g) | Glycolide (g) | Dehydrated PEG (g) | Structure of copolymer (—) | Weight average molecular weight according to GPC method (—) | Tensile modulus of the film (MPa) |
|---|---|---|---|---|---|---|
| Synthesis example 1 | 4.96 | 1.66 | 2.88 | PLGA-PEG-PLGA | 22000 | 57 |
| Synthesis example 2 | 1.92 | 0.96 | 2.88 | PLGA-PEG | 14000 | 2.1 |

Example 1

The water insoluble polymer obtained in Synthesis example 1 and the water insoluble copolymer obtained in Synthesis example 2 were mixed in a weight ratio of 70:30 and dissolved in dichloromethane. This was dropped into aqueous solution of 1 wt % polyvinyl alcohol (Cat. No. 360627, produced by Aldrich Corp.) to carry out a drying-in-O/W liquid, and a spherical particle dispersion was obtained.

Subsequently, after a wet fractionation by nylon sieves (cut off particle diameter: 65 μm, 185 μm, 260 μm, 360 μm and 540 μm), it was vacuum dried to obtain dried spherical particles with no aggregation or cohesion. Among the above-mentioned cut off particle diameters, respective 40 mg particles collected by sieves of the 4 kinds of size except 540 μm were dispersed in PBS 1 mL, respectively, and average particle diameter and particle size distribution were determined, and it was found to be, for the respective particles collected by the sieves of the 4 kinds of size, 125±60 μm, 220±40 μm, 310±50 μm and 450±90 μm, respectively.

For the above-mentioned particle dispersions, passing abilities through catheter were evaluated and it was found that the particles of which average particle diameter was 125 μm or 220 μm can be injected without resistance, and particles of which average particle diameter was 310 μm or 450 μm can also pass through the catheter tube, although a slight resistance was observed.

After that, the catheter was cut and opened in longitudinal direction and its inside was visually inspected, but the spherical particle was not observed.

For the particle of average particle diameter 310 μm, compressive modulus was measured by compression tester MCT-W500 of Shimadzu Corp. and it was found to be 1.4±0.3 MPa.

Degradability of this particle after immersing in PBS for 28 days was evaluated, and it was found that, compared to before the immersion, residual weight ratio was 30% and ratio of weight average molecular weight was 70%.

Example 2

A spherical particle dispersion was obtained in the same way as Example 1 except changing the weight ratio of the water insoluble polymer obtained in Synthesis example 1 and the water insoluble polymer obtained in Synthesis example 2 to 50:50.

Subsequently, it was wet fractionated and vacuum dried in the same way as Example 1 to thereby obtain a dried spherical particle with no aggregation or cohesion. For these particles, average particle diameters and particle size distributions were measured and it was found to be, for the respective particles collected by the sieves of the 4 kinds of size, 125±60 μm, 220±40 μm, 310±50 μm, 450±90 μm, respectively.

The above-mentioned particle dispersions were injected to the same catheter as Example 1 from a syringe, and it was found that all particles of the average particle diameters could pass the catheter tube without resistance. After that, the catheter was cut and opened in longitudinal direction and its inside was visually inspected, but the spherical particle was not observed.

For the particle of average particle diameter 310 μm, compressive modulus was measured and it was found to be 2.0±0.5 MPa.

Degradability of this particle after immersing in PBS for 28 days was evaluated, and it was found that, compared to before the immersion, residual weight ratio was 30% and ratio of weight average molecular weight was 70%.

Example 3

A spherical particle dispersion was obtained in the same way as Example 1. Subsequently, after wet fractionation in the same way as Example 1, it was rinsed with aqueous solution of 5 wt % PEG (produced by Wako Pure Chemical Industries, Ltd., average molecular weight 4,000) 200 mL, vacuum dried, and obtained a spherical particle with no aggregation or cohesion. For this particle, average particle diameter and particle size distribution were determined, and it was found to be, for the respective particles collected by the sieves of the 4 kinds of size, 125±60 μm, 220±40 μm, 310±50 μm and 450±90 μm.

The above-mentioned particle dispersions were injected to the same catheter as Example 1 from a syringe, and it was found that the particles of which average particle diameter was 125 μm or 220 μm can be injected without resistance, and particles of which average particle diameter was 310 μm or 450 μm can also pass through the catheter tube, although a slight resistance was observed. After that, the catheter was cut and opened in longitudinal direction and its inside was visually inspected, but the spherical particle was not observed.

For the particle of average particle diameter 310 μm, compressive modulus was measured and it was found to be, 1.3±0.3 MPa.

Degradability of this particle after immersing in PBS for 28 days was evaluated, and it was found that, compared to before the immersion, residual weight ratio was 30% and ratio of weight average molecular weight was 70%.

As mentioned above, it was found that a spherical particle comprising a blend polymer of the water insoluble polymer and the water insoluble polymer can pass through a catheter tube of which inner diameter is smaller than the particle diameter.

Comparative Example 1

A spherical particle dispersion was obtained in the same way as Example 1 except using the water insoluble polymer obtained in Synthesis example 1 only.

Subsequently, after wet fractionation in the same way as Example 1, vacuum dried and obtained a dried spherical particle with no aggregation or cohesion. For this particle, average particle diameter and particle size distribution were determined, and it was found to be, for the respective particles collected by the sieves of the 4 kinds of size, 125±60 μm, 220±40 μm, 310±50 μm and 450±90 μm.

The above-mentioned particle dispersions were injected to the same catheter as Example 1 from a syringe, and it was found that the particles of which average particle diameter was 125 μm or 220 μm could be injected without resistance, but particles of which average particle diameter was 310 μm or 450 μm could not pass through the catheter tube. After that, the catheter was cut and opened in longitudinal direction and its inside was visually inspected, and the spherical particle was observed.

For the particle of average particle diameter 310 μm, compressive modulus was measured and it was found to be, 14.4±2.9 MPa.

Degradability of this particle after immersing in PBS for 28 days was evaluated, and it was found that, compared to before the immersion, residual weight ratio was 28%, and ratio of weight average molecular weight was 63%.

TABLE 2

| | | After immersing in PBS for 28 days | |
|---|---|---|---|
| | Compressive modulus (MPa) | Residual weight ratio (%) | Ratio of weight average molecular weight (%) |
| Example 1 | 1.4 ± 0.3 | 30 | 70 |
| Example 2 | 2.0 ± 0.5 | 30 | 70 |
| Example 3 | 1.3 ± 0.3 | 30 | 70 |
| Comparative example 1 | 14.4 ± 2.9 | 28 | 63 |

Synthesis Example 3

Under nitrogen flow, L-lactide (produced by Purac Biochem Ltd.) 4.96 g, glycolide (produced by Boehringer Ingelheim Co.) 1.66 g and dehydrated PEG (Sunbright DKH-20T produced by Nihon Yushi Kogyo Co.) 2.88 g were mixed in a flask and after dissolved and mixed at 150° C., a toluene solution 460 μL in which tin dioctanoate (produced by Wako Pure Chemical Industries, Ltd.) was dissolved so that its concentration was 0.1 mol/L was added and reacted to thereby obtain a copolymer having PLGA-PEG-PLGA structure. This copolymer was dissolved in chloroform and dropped into a greatly excessive amount of diethyl ether/acetone mixed liquid to obtain a white precipitate. Weight average molecular weight according to the above-mentioned GPC method was 58,000.

Synthesis Example 4

Under nitrogen flow, L-lactide (produced by Purac Biochem Ltd.) 1.42 g, glycolide (produced by Boehringer Ingelheim Co.) 1.44 g and dehydrated PEG (Sunbright MEH-20T produced by Nihon Yushi Kogyo Co.) 2.88 g were mixed in a flask and after dissolved and mixed at 150° C., a toluene solution 460 μL in which tin dioctanoate (produced by Wako Pure Chemical Industries, Ltd.) was dissolved so that its concentration was 0.1 mol/L was added and reacted to thereby obtain a copolymer having PLGA-PEG-PLGA structure. This copolymer was dissolved in chloroform and dropped into a greatly excessive amount of diethyl ether/acetone mixed liquid to obtain a white precipitate. Weight average molecular weight according to the above-mentioned GPC method was 42,000.

Example 4

The purified copolymers shown in Synthesis examples 3 and 4 were dissolved in dichloromethane in a weight ratio of 7:3, and obtained a spherical particle by drying-in-O/W liquid method. This spherical particle was vacuum dried, and then fractionated by a nylon mesh. This fractionated particle was immersed in physiological saline solution to obtain a dispersion containing the spherical particle. When its particle size distribution was measured, it was found that the volume average particle diameter was approximately 450 µm, the distribution width was the average particle diameter±90 µm and the maximum particle diameter was 540 µm. $^1$H-NMR of the particle was measured and the weight content ratio of polyethylene glycol with respect to poly (lactide/glycolide) copolymer was 0.61.

As a result of evaluation of passing ability of the particle through catheter, it was possible to inject it into catheter with no problem, and the particle shape passed through the tip portion was spherical. The particle having maximum diameter 540 µm was deformed 30% in the catheter, but the passed particle shape was spherical and it recovered to a diameter larger than the inner diameter of the catheter. Whereas, the above-mentioned spherical particle was added into a phosphate buffered saline (pH7.4), and after passing 28 days at 37□, a residual weight ratio to that of before the treatment was determined, and it was found to be 30%.

Example 5

A dispersion containing spherical particle was obtained in the same way as Example 4 except dissolving the purified copolymers shown in Synthesis examples 3 and 4 in dichloromethane in a weight ratio of 55:45. When its particle size distribution was measured, it was found that the volume average particle diameter was approximately 450 µm, the distribution width was the average particle diameter±90 µm and the maximum particle diameter was 540 µm. $^1$H-NMR of the particle was measured and the weight content ratio of polyethylene glycol with respect to poly (lactide/glycolide) copolymer was 0.69.

As a result of evaluation of passing ability through catheter, it was possible to inject it into catheter with no problem, and the particle shape passed through the tip portion was spherical. The particle having maximum diameter 540 µm was deformed 30% in the catheter, but the passed particle shape was spherical and it recovered to a diameter larger than the inner diameter of the catheter. Whereas, the above-mentioned spherical particle was added into a phosphate buffered saline (pH7.4), and after passing 28 days at 37□, a residual weight ratio to that of before the treatment was determined, and it was found to be 35%.

Example 6

A dispersion containing spherical particle was obtained in the same way Example 4 except dissolving the purified copolymers shown in Synthesis examples 3 and 4 in dichloromethane in a weight ratio of 65:35. When its particle size distribution was measured, it was found that the volume average particle diameter was approximately 450 µm, the distribution width was the average particle diameter±90 µm and the maximum particle diameter was 540 µm. $^1$H-NMR of the particle was measured and the weight content ratio of polyethylene glycol with respect to poly (lactide/glycolide) copolymer was 0.63.

As a result of evaluation of passing ability through catheter, it was possible to inject it into catheter with no problem, and the particle shape passed through the tip portion was spherical. The particle having maximum diameter 540 µm was deformed 30% in the catheter, but the passed particle shape was spherical and it recovered to a diameter larger than the inner diameter of the catheter. Whereas, the above-mentioned spherical particle was added into a phosphate buffered saline (pH7.4), and after passing 28 days at 37□, a residual weight ratio to that of before the treatment was determined, and it was found to be 30%.

Comparative Synthesis Example 1

Under nitrogen flow, L-lactide (produced by Purac Biochem Ltd.) 40.3 g and tin dioctanoate (produced by Wako Pure Chemical Industries, Ltd.) 8.1 mg were added in a flask and reacted at 140° C. to thereby obtain poly (L-lactide). The obtained polymer was dissolved in chloroform and dropped into a greatly excessive amount of methanol to obtain a white precipitate. Weight average molecular weight according to GPC method was 70,000.

Comparative Example 2

A dispersion containing spherical particles was obtained in the same way as Example 4 except dissolving the polymer obtained in Comparative synthesis example 1 in dichloromethane. When its particle size distribution was measured, it was found that the volume average particle diameter was approximately 450 µm, the distribution width was the average particle diameter±90 µm and the maximum particle diameter was 540 µm. $^1$H-NMR of the particle was measured and the weight content ratio of polyethylene glycol with respect to poly (lactide/glycolide) copolymer was 0.00.

As a result of evaluation of passing ability through catheter of the spherical particle dispersion of this poly (L-lactide), injection became impossible just after starting injection due to a big resistance. There were some particles passed through the tip portion, but almost all particles could not pass the microcatheter. In addition, when it was injected to a catheter produced by Cordis Corp., MASS TRANSIT (total length is approximately 1,400 mm, inner diameter of tip portion is approximately 680 µm), injection became impossible just after starting injection due to a big resistance. There were some particles passed through the tip portion, but almost all particles could not pass the microcatheter. Whereas, the above-mentioned spherical particle was added into a phosphate buffered saline (pH7.4), and after passing 28 days at 37° C., a residual weight ratio to that of before the treatment was determined, and it was found to be 98%.

Comparative Synthesis Example 2

Under nitrogen flow, L-lactide (produced by Purac Biochem Ltd.) 40.3 g and dehydrated polyethylene glycol (DKH-80H, produced by Nihon Yushi Co.) of average molecular weight 8,000, 8.3 g were melted and mixed at 140° C. in a flask and then tin dioctanoate (produced by Wako Pure Chemical Industries, Ltd.) 8.1 mg was added and reacted at 180° C. to thereby obtain an A-B-A type copolymer (PLA-PEG-PLA). The obtained polymer was dissolved in chloroform and dropped into a greatly excessive amount of methanol to obtain a white precipitate. Weight average molecular weight according to GPC method was approximately 47,000.

Comparative example 3

A dispersion containing spherical particles was obtained in the same way as Example 4 except dissolving the above-mentioned purified copolymer in dichloromethane. When particle size distribution was measured, it was found that the volume average particle diameter was approximately 450 μm, the distribution width was the average particle diameter±90 μm and the maximum particle diameter was approximately 540 μm. ¹H-NMR of the particle was measured and the weight content ratio of polyethylene glycol with respect to polylactide was 0.11. As a result of evaluation of passing ability through catheter, injection became impossible just after starting injection due to a big resistance. There were some particles passed through the tip portion, but almost all particles could not pass the microcatheter. And, when it was injected to a catheter produced by Cordis Corp., MASS TRANSIT (total length is approximately 1,400 mm, inner diameter of tip portion is approximately 680 μm), injection became impossible just after starting injection due to a big resistance. There were some particles passed through the tip portion, but almost all particles could not pass the microcatheter. Whereas, the above-mentioned spherical particle was added into a phosphate buffered saline (pH7.4), and after passing 28 days at 37° C., a residual weight ratio to that of before the treatment was determined, and it was found to be 98%.

Comparative Example 4

A dispersion containing spherical particles was obtained in the same way as Example 4 except dissolving the purified copolymer shown in Synthesis examples 3 and 4 in dichloromethane in a weight ratio of 3:7. When particle size distribution was measured, it was found that the volume average particle diameter was approximately 450 μm, the distribution width was the average particle diameter±90 μm and the maximum particle diameter was approximately 540 μm. ¹H-NMR of the particle was measured and the weight content ratio of polyethylene glycol with respect to poly (lactide/glycolide) copolymer was 0.83.

As a result of evaluation of passing ability through catheter, it was possible to inject into catheter with no problem. However, particles passed through the catheter were deformed and crushed, and sphericity was not remained. Whereas, the above-mentioned spherical particle was added into a phosphate buffered saline (pH7.4), and after passing 28 days at 37° C., a residual weight ratio to that of before the treatment was determined, and it was found to be 40%.

Comparative Example 5

The purified copolymer shown in Synthesis example 4 was dissolved in dichloromethane and was tried to prepare a spherical particle by drying-in-O/W liquid method, but the particle did not become spherical. From this particle, a dispersion containing particle was obtained in the same way as Example 4. When particle size distribution was measured, it was found that the volume average particle diameter was approximately 450 μm, the distribution width was the average particle diameter±90 μm and the maximum particle diameter was approximately 540 μm. ¹H-NMR of the particle was measured and the weight content ratio of polyethylene glycol with respect to poly (lactide/glycolide) copolymer was 1.04.

As a result of evaluation of passing ability through catheter, it was possible to inject into catheter with no problem. However, particles passed through the catheter were deformed and crushed, and sphericity was not remained. Whereas, the above-mentioned spherical particle was added into a phosphate buffered saline (pH7.4), and after passing 28 days at 37° C., a residual weight ratio to that of before the treatment was determined, and it was found to be 40%.

TABLE 3

|  | L-lactide (g) | Glycolide (g) | Dehydrated PEG (g) | Structure of copolymer (—) | Weight average molecular weight according to GPC method (—) |
| --- | --- | --- | --- | --- | --- |
| Synthesis example 3 | 4.96 | 1.66 | 2.88 | PLGA-PEG-PLGA | 58000 |
| Synthesis example 4 | 1.42 | 1.44 | 2.88 | PLGA-PEG-PLGA | 42000 |
| Comparative synthesis example 1 | 40.3 | 0.00 | 0.00 | PLA | 70000 |
| Comparative synthesis example 2 | 40.3 | 0.00 | 8.30 | PLA-PEG-PLA | 47000 |

TABLE 4

|  | Structure of copolymer | Average particle diameter (μm) | Particle size distribution (Average particle diameter ± μm) | Maximum particle diameter (μm) | Residual weight ratio after immersing in PBS for 28 days (%) | Containing ratio of said water-soluble polymer to said biodegradable polymer (—) | Passing ability through catheter |
| --- | --- | --- | --- | --- | --- | --- | --- |
| Example 4 | PLGA-PEG-PLGA | 450 | ±90 | 540 | 30 | 0.61 | ○ |
| Example 5 | PLGA-PEG-PLGA | 450 | ±90 | 540 | 35 | 0.69 | ○ |
| Example 6 | PLGA-PEG-PLGA | 450 | ±90 | 540 | 30 | 0.63 | ○ |
| Comparative example 2 | PLA | 450 | ±90 | 540 | 98 | 0.00 | x |
| Comparative example 3 | PLA-PEG-PLA | 450 | ±90 | 540 | 98 | 0.11 | x |

TABLE 4-continued

|  | Structure of copolymer | Average particle diameter (μm) | Particle size distribution (Average particle diameter ± μm) | Maximum particle diameter (μm) | Residual weight ratio after immersing in PBS for 28 days (%) | Containing ratio of said water-soluble polymer to said biodegradable polymer (—) | Passing ability through catheter |
|---|---|---|---|---|---|---|---|
| Comparative example 4 | PLGA-PEG-PLGA | 450 | ±90 | 540 | 40 | 0.83 | Δ |
| Comparative example 5 | PLGA-PEG-PLGA | 450 | ±90 | 540 | 40 | 1.04 | Δ |

Passing ability through catheter
◯: The injection became possible without resistance and Particle after passing was spherical.
Δ: The injection became possible without resistance, but Particle after passing was not spherical.
×: The injection became impossible.

Synthesis Example 5

Under nitrogen flow, L-lactide (produced by Purac Biochem Ltd.) 6.6 g and dehydrated PEG (Sunbright DKH-20T produced by Nihon Yushi Kogyo Co.) 2.9 g were mixed in a flask and after dissolved and mixed at 150° C., a toluene solution 460 μL in which tin dioctanoate (produced by Wako Pure Chemical Industries, Ltd.) was dissolved so that its concentration was 0.1 mol/L was added and reacted to thereby obtain a copolymer having PLGA-PEG-PLGA structure. This copolymer was dissolved in chloroform and dropped into a greatly excessive amount of diethyl ether/acetone mixed liquid to obtain a white precipitate. Weight average molecular weight according to the above-mentioned GPC method was 15,000.

Example 7

The purified copolymer obtained in Synthesis example 5, 1.0 g was dissolved in dichloromethane 30 mL, dropped in aqueous solution of 1 wt % polyvinyl alcohol (Cat. No. 360627, produced by Aldrich Corp.), and by carrying out drying-in-O/W liquid, a spherical particle dispersion was obtained. The supernatant of this dispersion was replaced by decantation with 10 wt % of aqueous solution of PEG (produced by Wako Pure Chemical Industries, Ltd. average molecular weight 600), and stirred for 30 minutes. Subsequently, after wet fractionation by nylon sieves, it was vacuum dried to obtain a dried spherical particle. The surface of the particle was in a gel state.

When particle size distribution for this particle 40 mg was measured, it was as shown in Table 6. When passing ability through catheter of this particle dispersion was evaluated by the above-mentioned way, it was possible to inject with no resistance. After that, the catheter was cut and opened in longitudinal direction and its inside was visually inspected, but the spherical particle was not observed.

Result of evaluation of degradability of this particle after immersion in PBS for 28 days is shown in Table 6.

Furthermore, after wet fractionation by nylon sieves, a particle dispersion was obtained by immersing the particle obtained by vacuum drying in physiological saline solution. Subsequently, after inserting a 24 G indwelling needle into femoral vein of 2 rats of 10 weeks of age put under anesthesia by Nembtal, this spherical particle dispersion was injected through a catheter. After 28 days, when a visual inspection of lung, and preparing an tissue section and an observation of the tissue section after injection of the spherical particle dispersion were carried out and, pulmonary infarction was observed in both of them, and furthermore, degradation of the particle could be confirmed.

Example 8

The spherical particle dispersion obtained by the drying-in-O/W liquid in Example 7 was, after a wet fractionation by a nylon sieve, rinsed with approximately 200 mL aqueous solution of 10 wt % PEG (produced by Wako Pure Chemical Industries, Ltd. average molecular weight 600), and vacuum dried to obtain a dried spherical particle. The surface of the particle was in a gel state.

Particle size distribution of this particle was measured and the result was shown in Table 6. When passing ability through catheter of this particle dispersion was evaluated by the above-mentioned way, it was possible to inject with no pressure drop. After that, the catheter was cut and opened in longitudinal direction and its inside was visually inspected, but the spherical particle was not observed.

Furthermore, result of evaluation of degradability of this particle after immersion in PBS for 28 days is shown in Table 6.

Example 9

The spherical particle-dispersion obtained by the drying-in-O/W liquid in Example 7 was, after a wet fractionation by a nylon sieve, rinsed with approximately 200 mL aqueous solution of 1 wt % PEG (produced by Wako Pure Chemical Industries, Ltd. average molecular weight 1,000), and vacuum dried to obtain a dried spherical particle. The particle surface was dried and smooth.

Particle size distribution of this particle was measured and the result was shown in Table 6. When passing ability of this particle dispersion was evaluated by injecting into a catheter, it was possible to inject with no resistance. After that, the catheter was cut and opened in longitudinal direction and its inside was visually inspected, but the spherical particle was not observed.

Furthermore, result of evaluation of degradability of this particle after immersion in PBS for 28 days is shown in Table 6.

Example 10

The spherical particle dispersion obtained by the drying-in-O/W liquid in Example 7 was, after a wet fractionation by a nylon sieve, rinsed with approximately 200 mL aqueous solution of 1 wt % PEG (produced by Wako Pure Chemical Industries, Ltd. average molecular weight 1,000), and vacuum dried to obtain a dried spherical particle. The particle surface was dried and smooth.

Particle size distribution of this particle was measured and the result was shown in Table 6. When passing ability through catheter of this particle dispersion was evaluated by the above-mentioned way, it was possible to inject with no resistance. After that, the catheter was cut and opened in longitudinal direction and its inside was visually inspected, but the spherical particle was not observed.

Furthermore, result of evaluation of degradability of this particle after immersion in PBS for 28 days is shown in Table 6.

Example 11

The spherical particle dispersion obtained by the drying-in-O/W liquid in Example 7 was, after a wet fractionation by a nylon sieve, rinsed with approximately 200 mL aqueous solution of 3 wt % PEG (produced by Wako Pure Chemical Industries, Ltd. average molecular weight 1,000), and vacuum dried to obtain a dried spherical particle. The particle surface was dried and smooth.

Particle size distribution of this particle was measured and the result was shown in Table 6. When passing ability through catheter of this particle dispersion was evaluated by the above-mentioned way, it was possible to inject with no resistance. After that, the catheter was cut and opened in longitudinal direction and its inside was visually inspected, but the spherical particle was not observed.

Furthermore, an evaluation result of degradability of this particle after immersion in PBS for 28 days is shown in Table 6.

Example 12

The spherical particle dispersion obtained by the drying-in-O/W liquid in Example 7 was, after a wet fractionation by a nylon sieve, rinsed with approximately 200 mL aqueous solution of 3 wt % PEG (produced by Wako Pure Chemical Industries, Ltd. average molecular weight 1,000), and vacuum dried to obtain a dried spherical particle. The particle surface was dried and smooth.

Particle size distribution of this particle was measured and the result was shown in Table 6. When passing ability through catheter of this particle dispersion was evaluated by the above-mentioned way, it was possible to inject with no resistance. After that, the catheter was cut and opened in longitudinal direction and its inside was visually inspected, but the spherical particle was not observed.

Furthermore, an evaluation result of degradability of this particle after immersion in PBS for 28 days is shown in Table 6.

Example 13

The spherical particle dispersion obtained by the drying-in-O/W liquid in Example 7 was, after a wet fractionation by a nylon sieve, rinsed with approximately 200 mL aqueous solution of 20 wt % PEG (produced by Wako Pure Chemical Industries, Ltd. average molecular weight 1,000), and vacuum dried to obtain a dried spherical particle. The particle surface was dried and smooth.

Particle size distribution of this particle was measured and the result was shown in Table 6. When passing ability through catheter of this particle dispersion was evaluated by the above-mentioned way, it was possible to inject with no resistance. After that, the catheter was cut and opened in longitudinal direction and its inside was visually inspected, but the spherical particle was not observed.

Furthermore, an evaluation result of degradability of this particle after immersion in PBS for 28 days is shown in Table 6.

Example 14

The spherical particle dispersion obtained by the drying-in-O/W liquid in Example 7 was, after a wet fractionation by a nylon sieve, rinsed with approximately 200 mL aqueous solution of 5 wt % PEG (produced by Wako Pure Chemical Industries, Ltd. average molecular weight 4,000), and vacuum dried to obtain a dried spherical particle. The particle surface was dried and smooth.

Particle size distribution of this particle was measured and the result was shown in Table 6. When passing ability through catheter of this particle dispersion was evaluated by the above-mentioned way, it was possible to inject with no resistance. After that, the catheter was cut and opened in longitudinal direction and its inside was visually inspected, but the spherical particle was not observed.

Furthermore, an evaluation result of degradability of this particle after immersion in PBS for 28 days is shown in Table 6.

Synthesis Example 6

Under nitrogen flow, L-lactide (produced by Purac Biochem Ltd.) 5.0 g, glycolide (produced by Boehringer Ingelheim Co.) 1.7 g and dehydrated PEG (Sunbright DKH-20T produced by Nihon Yushi Kogyo Co.) 2.9 g were mixed in a flask, and after dissolved and mixed at 150° C., a toluene solution 490 µL in which tin dioctanoate (produced by Wake Pure Chemical Industries, Ltd.) was dissolved so that its concentration was 0.1 mol/L was added and reacted, to thereby obtain a copolymer having PLGA-PEG-PLGA structure. This copolymer was dissolved in chloroform and dropped in greatly excessive amount of diethyl ether/acetone mixed liquid and obtained a white precipitate. Weight average molecular weight by GPC method was 22,000.

Example 15

In the same way as Example 7, a spherical particle dispersion was obtained by dissolving the above-mentioned purified copolymer 0.5 mg in dichloromethane 19 mL, dropping it in an aqueous solution of 1 wt % polyvinyl alcohol, and carrying out a drying-in-O/W liquid. After a wet fractionation by a nylon sieve, this dispersion was rinsed with approximately 200 mL aqueous solution of 5 wt % PEG (produced by Wako Pure Chemical Industries, Ltd. average molecular weight 1,000), vacuum dried, and obtained a uniformly shaped dried spherical particle. The particle surface was dried and smooth.

Particle size distribution of this particle was measured and the result was shown in Table 6. When passing ability through catheter of this particle dispersion was evaluated by the above-mentioned way, it was possible to inject with no resistance. After that, the catheter was cut and opened in longitudinal direction and its inside was visually inspected, but the spherical particle was not observed.

Result of evaluation of degradability of this particle after immersion in PBS for 28 days is shown in Table 6.

Furthermore, after a wet fractionation by a nylon sieve, this particle was vacuum dried, and a particle dispersion was obtained by immersing the obtained particle in physiological saline solution. Subsequently, after inserting a 24 G indwelling needle into femoral vein of 2 rats of 10 weeks of age put under anesthesia by Nembtal, this spherical particle dispersion was injected through a catheter. After 28 days, when a visual inspection of lung, preparing an tissue section and an observation of the tissue section after injection of the spherical particle dispersion were carried out and, pulmonary infarction was observed in both of them, and furthermore, degradation of the particle could be confirmed.

Example 16

The spherical particle dispersion obtained by the drying-in-O/W liquid in Example 15 was, after a wet fractionation by a nylon sieve, rinsed with approximately 200 mL aqueous solution of 5 wt % PEG (produced by Wako Pure Chemical Industries, Ltd. average molecular weight 1,000), vacuum dried, and obtained a uniformly shaped dried spherical particle. The particle surface was dried and smooth.

Particle size distribution of this particle was measured and the result was shown in Table 6. When passing ability through catheter of this particle dispersion was evaluated by the above-mentioned way, it was possible to inject with no resistance. After that, the catheter was cut and opened in longitudinal direction and its inside was visually inspected, but the spherical particle was not observed.

Furthermore, an evaluation result of degradability of this particle after immersion in PBS for 28 days is shown in Table 6.

From the above, it was found that a particle of which surface is coated with PEG can be molded without an aggregation or cohesion, and it can pass through a microcatheter without resistance or clogging.

Comparative Example 6

The spherical particle dispersion obtained by the drying-in-O/W liquid in Example 7 was, after a wet fractionation by a nylon sieve, vacuum dried to obtain a dried spherical particle.

Particle size distribution of this particle was measured and the result was shown in Table 6. Passing ability through catheter of this particle dispersion was evaluated according to the above-mentioned way, but after starting injection, the spherical particle aggregated around connector portion of the catheter inlet, and the injection became impossible with a strong resistance.

Comparative Example 7

The spherical particle dispersion obtained by the drying-in-O/W liquid in Example 7 was, after a wet fractionation by a nylon sieve, vacuum dried to obtain a dried spherical particle.

PEG (produced by Wako Pure Chemical Industries, Ltd. average molecular weight 1000) 10 mg was dissolved and stirred in this dispersion and particle size distribution of this particle was measured and the result was shown in Table 6. Passing ability through catheter of this particle dispersion was evaluated according to the above-mentioned way, but after starting injection, the spherical particle aggregated around connector portion of the catheter inlet, and the injection became impossible with a strong resistance.

Comparative Example 8

The spherical particle dispersion obtained by the drying-in-O/W liquid in Example 8 was, after a wet fractionation by a nylon sieve, vacuum dried to obtain a dried spherical particle.

Particle size distribution of this particle was measured and the result was shown in Table 6. Passing ability through catheter of this particle dispersion was evaluated according to the above-mentioned way, but after starting injection, the spherical particle aggregated around connector portion of the catheter inlet, and the injection became impossible with a strong resistance.

Comparative Example 9

The spherical particle dispersion obtained by the drying-in-O/W liquid in Example 9 was, after a wet fractionation by a nylon sieve, vacuum dried to obtain a dried spherical particle.

Particle size distribution of this particle was measured and the result was shown in Table 6. Passing ability through catheter of this particle dispersion was evaluated according to the above-mentioned, but after starting injection, the spherical particle aggregated around connector portion of the catheter inlet, and the injection became impossible with a strong resistance.

Comparative Example 10

The spherical particle dispersion obtained by drying-in-O/W liquid in Example 15 was, after a wet fractionation by a nylon sieve, vacuum dried and obtained a dried particle in which particles aggregated or cohered with each other coexisted.

Particle size distribution of a particle from this dried particle of which particle diameter approximately 300 μm which is not aggregated or cohered was measured and the result was shown in Table 6. Passing ability through catheter of this particle dispersion was evaluated according to the above-mentioned way, but after starting injection, the spherical particle aggregated around connector portion of the catheter inlet, and the injection became impossible with a strong resistance.

TABLE 5

|  | L-lactide (g) | Glycolide (g) | Dehydrated PEG (g) | Structure of copolymer (—) | Weight average molecular weight according to GPC method (—) |
| --- | --- | --- | --- | --- | --- |
| Synthesis example 5 | 6.6 | 0.0 | 2.9 | PLA-PEG-PLA | 15000 |
| Synthesis example 6 | 5.0 | 1.7 | 2.9 | PLGA-PEG-PLGA | 22000 |

TABLE 6

| | Structure of copolymer | Existence or nonexistence of aggregation or cohesion of vacuum dried spherical particle | Average particle diameter (μm) | Particle size distribution (Average particle diameter ± μm) | PEG Coating | | After immersing in PBS for 28 days | | Passing ability through catheter |
|---|---|---|---|---|---|---|---|---|---|
| | | | | | Average molecular weight of PEG (Mw.) | Density of PEG in aqueous solution (wet %) | Residual weight ratio (%) | Ratio of weight average molecular weight (%) | |
| Example 7 | PLA-PEG-PLA | Nonexistence | 125 | ±60 | 600 | 10 | 69 | 31 | ○ |
| Example 8 | PLA-PEG-PLA | Nonexistence | 220 | ±50 | 600 | 10 | 68 | 31 | ○ |
| Example 9 | PLA-PEG-PLA | Nonexistence | 125 | ±60 | 1000 | 1 | 68 | 31 | ○ |
| Example 10 | PLA-PEG-PLA | Nonexistence | 220 | ±50 | 1000 | 1 | 67 | 31 | ○ |
| Example 11 | PLA-PEG-PLA | Nonexistence | 220 | ±50 | 1000 | 3 | 67 | 31 | ○ |
| Example 12 | PLA-PEG-PLA | Nonexistence | 310 | ±50 | 1000 | 3 | 72 | 33 | ○ |
| Example 13 | PLA-PEG-PLA | Nonexistence | 450 | ±90 | 1000 | 20 | 80 | 35 | ○ |
| Example 14 | PLA-PEG-PLA | Nonexistence | 220 | ±50 | 4000 | 5 | 69 | 32 | ○ |
| Example 15 | PLGA-PEG-PLGA | Nonexistence | 110 | ±105 | 1000 | 5 | 30 | 62 | ○ |
| Example 16 | PLGA-PEG-PLGA | Nonexistence | 310 | ±50 | 1000 | 5 | 32 | 64 | ○ |
| Comparative example 6 | PLA-PEG-PLA | Nonexistence | 220 | ±50 | — | — | — | — | x |
| Comparative example 7 | PLA-PEG-PLA | Nonexistence | 220 | ±50 | — | — | — | — | x |
| Comparative example 8 | PLA-PEG-PLA | Nonexistence | 310 | ±50 | — | — | — | — | x |
| Comparative example 9 | PLA-PEG-PLA | Nonexistence | 450 | ±90 | — | — | — | — | x |
| Comparative example 10 | PLGA-PEG-PLGA | Existence partially | 310 | ±50 | — | — | — | — | x |

All PEG used for coating were produced by Wako Pure Chemical Industries, Ltd
○: Pass
x: Causing resistance or clogging
—: No Coating

The invention claimed is:

1. A method for producing a biodegradable particle, the method consisting of:
   providing a water insoluble polymer A, wherein said water insoluble polymer A is a block copolymer including a water-soluble polymer block and a biodegradable polymer block, and has a weight ratio of the water-soluble polymer block of 50% or more, and a tensile modulus of the water insoluble polymer A is 1 MPa or more and less than 50 MPa measured when the water insoluble polymer A is in the form of a film A in a water saturated state;
   providing a water insoluble polymer B, wherein said water insoluble polymer B is a block copolymer including a water-soluble polymer block and a biodegradable polymer block, and has a weight ratio of the water-soluble polymer block of less than 50%, and a tensile modulus of the water insoluble polymer B is 50 MPa or more measured when the water insoluble polymer B is in the form of a film B in a water saturated state;
   mixing polymer A and polymer B;
   forming an oil in water (o/w) emulsion of said mixture in water with a surface active agent; and
   drying said o/w emulsion to form a biodegradable particle comprising polymer A and polymer B;
   wherein said biodegradable particle has an average particle diameter of 100 μm or more; and
   wherein, when passed through a catheter having an inner diameter of 60% or more and 85% or less of the particle diameter while in a water saturated state, the biodegradable particle recovers its shape to have a particle diameter is larger than the inner diameter of the catheter.

2. A method for producing a biodegradable particle according to claim 1 characterized in that a blend ratio of said water insoluble polymer B is 20 wt % or more.

3. A biodegradable particle produced by the method of claim 1.

4. A biodegradable particle produced by the method of claim 2.

* * * * *